United States Patent [19]

Hall

[11] Patent Number: 4,906,844
[45] Date of Patent: Mar. 6, 1990

[54] PHASE SENSITIVE OPTICAL MONITOR FOR THIN FILM DEPOSITION

[75] Inventor: Randolph L. Hall, Newbury Park, Calif.

[73] Assignee: Rockwell International Corporation, El Segundo, Calif.

[21] Appl. No.: 231,795

[22] Filed: Aug. 12, 1988

[51] Int. Cl.[4] .............................................. G02F 1/01
[52] U.S. Cl. .................................... 250/225; 356/369
[58] Field of Search ...................... 250/225; 350/150; 356/369, 368, 367, 381

[56] References Cited

U.S. PATENT DOCUMENTS

| | | | |
|---|---|---|---|
| 2,338,234 | 1/1944 | Dimmick | 427/10 |
| 3,880,524 | 4/1975 | Dill et al. | 250/225 |
| 4,053,232 | 10/1977 | Dill et al. | 356/369 |
| 4,105,338 | 8/1978 | Kuroha | 356/365 |
| 4,176,951 | 12/1979 | Robert et al. | 356/365 |
| 4,585,348 | 4/1986 | Chastang et al. | 356/369 |
| 4,653,924 | 3/1987 | Itonaga et al. | 356/369 |
| 4,668,860 | 5/1987 | Anthon | 250/225 |
| 4,672,196 | 6/1987 | Canino | 250/225 |
| 4,707,611 | 11/1987 | Southwell | 250/571 |

OTHER PUBLICATIONS

Budde, Photoelectric Analysis of Polarized Light, Applied Optics, vol. 1, p. 201 (1962).

Hauge, et al., Design and Operation of ETA, an Automated Ellipsometer, IBM Journal of Research & Development, p. 472 (Nov. 1973).

Hottier, et al., In Situ Monitoring by Ellipsometry of Metalorganic Epitaxy of GaAlAs-GaAs Superlattice, Journal of Applied Physics, vol. 51, p. 1599 (1980).

Netterfield, et al., Characterization of Growing Thin Films by In Situ Ellipsometry, Spectral Reflectance and Transmittance Measurements, and Ion-Scattering Spectroscopy, Review of Scientific Instruments, vol. 56, p. 1995 (1985).

Theeten, et al., Ellipsometric Assessment of (Ga,Al) As/GaAs Epitaxial Layers During Their Growth in Organometallic VPE System, Journal of Crystal Growth, vol. 46, p. 245 (1979).

Primary Examiner—David C. Nelms
Attorney, Agent, or Firm—H. Frederick Hamann; John J. Deinken

[57] ABSTRACT

The thickness of growing thin film layer is monitored by directing a beam of circularly polarized monochromatic monitoring light into the layer and detecting the portion of the monitoring light reflected from the layer. The difference in phase between the s and p polarized components of the reflected light is measured and those thicknesses of the layer at which the difference in phase between the s and p components is zero are related to thicknesses which are an integral multiple of one fourth of the wavelength of the monitoring light in the layer. An apparatus for monitoring the thickness of a growing layer during the fabrication of an optical thin film includes a source of light for directing a beam of light at the growing layer and a polarizer between the source and the layer for converting the light beam to a linearly polarized beam. A quarterwave plate between the polarizer and the layer converts the linearly polarized beam to a circularly polarized beam, while a polarizing beam splitter receives the portion of the beam reflected from the layer and divides the portion into a +45° polarized component and a −45° polarized component. A first detector detects the intensity of the +45° polarized component and a second detector detects the intensity of the −45° polarized component.

2 Claims, 4 Drawing Sheets

PHASE SENSITIVE OPTICAL MONITOR FOR THIN FILM DEPOSITION

BACKGROUND OF THE INVENTION

This invention relates to the design and fabrication of optical coatings for controlling the manner in which light of particular wavelengths is transmitted by or reflected from an optical surface.

Optical coatings are made possible by the principles of optical interference, which describe the modifications in the transmitted and reflected intensities of light when two or more beams of light are superposed. The brilliant colors, for example, which may be seen when light is reflected from a soap bubble or from a thin layer of oil floating on water are produced by interference effects between two trains of light waves reflected at opposite surfaces of the thin soap or oil film.

One important practical application for these interference effects in thin films involves the production of coated optical surfaces. If a film of a transparent substance is deposited on a lens, for example, with a refractive index which is properly selected according to the refractive index of the lens material and with a thickness which is one quarter of a particular wavelength of light in the film, the reflection of that wavelength of light from the lens surface can be almost completely suppressed. The light which would otherwise be reflected is not absorbed by such an antireflecting film; rather, the energy in the incident light is redistributed so that a decrease in reflection is accompanied by a concomitant increase in the intensity of the light which is transmitted. The beneficial effects of thin film coatings, such as antireflection, are so desirable that substantially all high quality optical components are provided with them.

As the optical coating art developed, considerable improvements were achieved in the antireflective performance of such film with the introduction of composite films having two or more superimposed layers. This approach provided the flexibility to design a wide range of multiple-layer interference coatings for implementing a great variety of transmission and reflection spectrums. As a result, complex spectral filter structures were added to a large number of new optical devices. Antireflection coatings, laser dielectric mirrors, television camera edge filters, optical bandpass filters, and band-rejection filters are some of the examples of useful devices employing multilayer thin-film interference coatings. Two different materials are typically used in fabricating such a composite film, one with a relatively high index of refraction and the other with a relatively low index of refraction. The two materials are alternately deposited in a controlled sequence of thicknesses to obtain the desired optical characteristics for the film. The deposition process is typically controlled by monitoring the thickness of each layer as it is deposited and terminating the deposition when the layer reaches the correct thickness.

Practical realizations of these complex designs, however, have been inhibited by the limitations of thin film fabrication technology, which make it difficult to ensure that a fabricated coating accurately implements the theoretically specified refractive index profile. One of the problems which has been associated with traditional thin film growth monitoring techniques is the tendency for thickness errors to accumulate over the course of a growth cycle. Many thin film devices are fabricated using layers which are multiples of a quarter wave optical thickness. The standard practice in the prior art is to monitor the growth of such layers using light at the wavelength for which the device is designed. Consequently, when the thickness of the layer reaches each quarter wave point, the reflectance of the monitoring light from the layer will be at a maximum or minimum. These "turning points" are used to control the deposition of the layers. Because it is difficult to determine precisely where a maximum or minimum occurs when approaching such an event in real time, a need has developed in the art for a thin film monitoring procedure which can provide a highly accurate indication of the points at which such quarter wave thicknesses are reached during the deposition process.

SUMMARY OF THE INVENTION

This invention makes it possible to readily determine, with a high degree of accuracy, the points at which the thickness of a growing thin film corresponds to integral multiples of one fourth the wavelength of a monitoring beam of light.

A method of monitoring the thickness of a growing layer during the fabrication of an optical thin film includes, according to this invention, the steps of directing a beam of circularly polarized monochromatic monitoring light into the layer and detecting the portion of the monitoring light reflected from the layer. The difference in phase between the s and p polarized components of the reflected light is measured and those thicknesses of the layer at which the difference in phase between the s and p components is zero are related to thicknesses which are an integral multiple of one fourth of the wavelength of the monitoring light in the layer for the angle of incidence of the monitor.

In a more particular embodiment, the step of measuring the difference in phase between the s and p polarized components involves dividing the portion of the monitoring light reflected from the layer into a component polarized at +45° with respect to the p polarization direction of the reflected light and a component polarized at −45° with respect to the p polarization direction of the reflected light. The intensities of the +45° and −45° polarized components are detected, then compared to determine the difference in phase between the s and p polarized components.

An apparatus for monitoring the thickness of a growing layer during the fabrication of an optical thin film includes, according to this invention, a source of light for directing a beam of light at the growing layer and a polarizer between the source and the layer for converting the light beam to a linearly polarized beam. A quarterwave plate between the polarizer and the layer converts the linearly polarized beam to a circularly polarized beam, while a polarizing beam splitter receives the portion of the beam reflected from the layer. The beam splitter is rotated about the axis of the reflected beam to divide the reflected beam into a component polarized at +45° with respect to the p polarization direction of the reflected beam and a component polarized at −45° with respect to the p polarization direction of the reflected beam. A first detector detects the intensity of the +45° polarized component and a second detector detects the intensity of the −45° polarized component.

In more particular embodiments, the source of light may be a source of monochromatic light or a monochromator may be placed between the source and the polarizer for selecting a particular wavelength of light.

DESCRIPTION OF THE INVENTION

Figure 1:
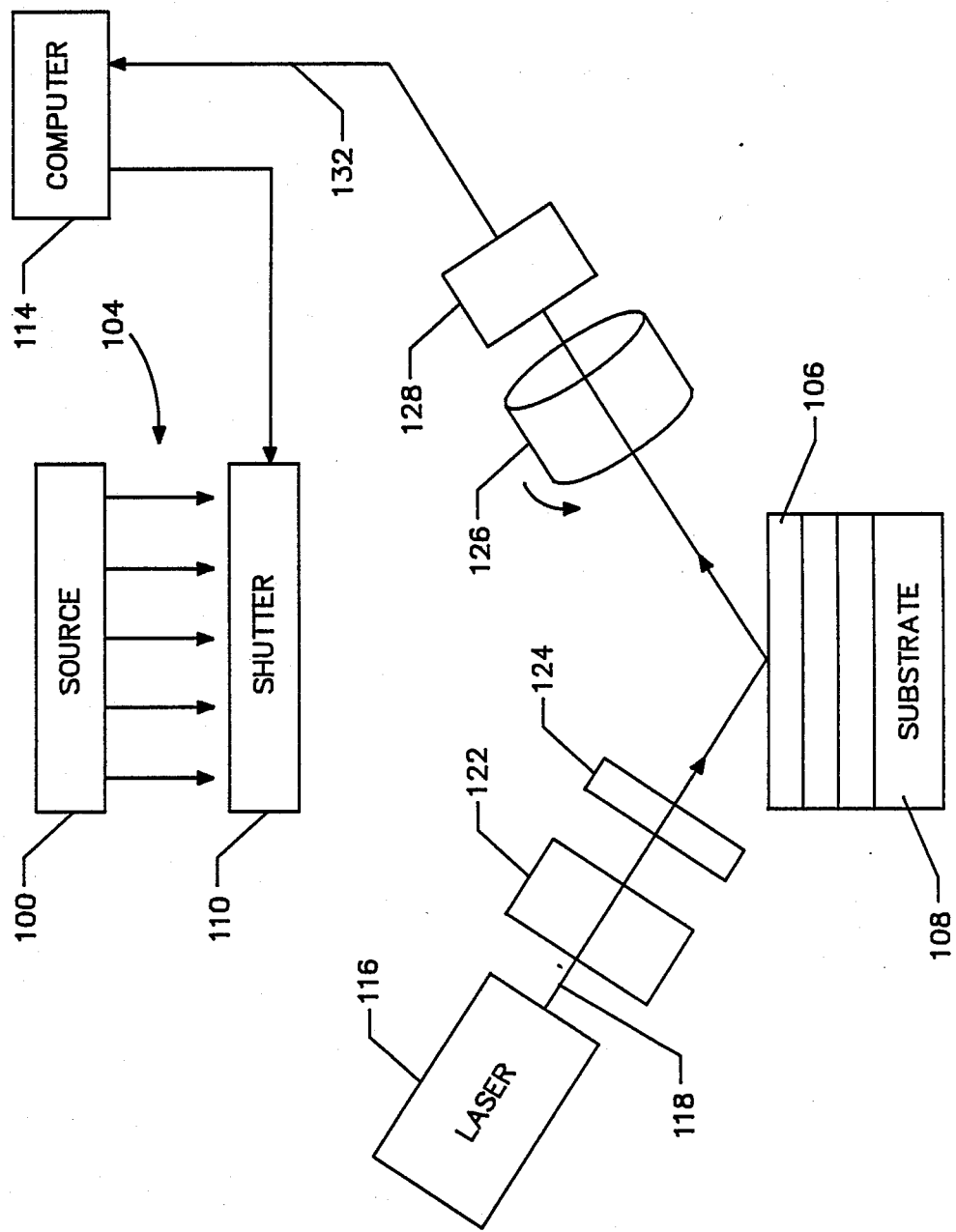
FIG. 1 depicts in schematic form an apparatus which can be employed in depositing thin films using the measurement technique of the invention.

The present invention enables ellipsometric or phase measurement methods to be used in real-time monitoring of the fabrication of complex filter structures with very thin layers. An ellipsometer is an instrument which analyzes the polarization state of an optical beam reflected from a surface. Changes in the polarization states of an initially linearly polarized beam yield information concerning the optical constants of the surface, including the thickness and index of any thin film on the surface. One example of an apparatus which can be employed in depositing thin films using the measurement technique of the invention is illustrated in schematic form in FIG. 1. A source 100 releases material, as indicated by the arrows 104, which is deposited in a thin film layer, such as the layer 106, on a substrate 108. The substrate can be shielded from the source material by a movable shutter 110, which is controlled by a computer 114. Although only a single source is shown in the drawing, those skilled in the art will appreciate that multiple sources and shutters can be used and controlled by the computer in order that layers with different compositions can be deposited. An ellipsometer, including a laser 116, a linear polarizer 122, a quarter wave plate 124, a rotating analyzer 126, and a detector 128, is used to monitor the thickness of the laser being deposited. Light 118 from the laser 116 passes through the linear polarizer 122 and emerges as linearly polarized light which is rendered circularly polarized by the quarter wave plate 124. The light is then directed toward the substrate 106 at a fixed angle of incidence. The light reflected from each layer interface on the substrate passes through the rotating analyzer 126 and is sensed by the detector 128. The computer 114 is programmed to monitor the output signal 132 from the detector and close the shutter 110 when the desired thickness for the layer 106 is reached. The modulated output $I(\theta)$ from the detector can be described, in the case of a rotating analyzer polarizer, by the relationship:

$$I(\theta) = I_0 (1 + A_2 \cos 2\theta + B_2 \sin 2\theta) \quad (1)$$

where $\theta$ is the angle of the rotating analyzer 126, $I_0$ is a constant, and $A_2$ and $B_2$ are the Fourier coefficients for the second harmonic frequency of the signal. All harmonics present in the data, other than the zeroth and the second, are due to noise or other error sources in the system. The $A_2$ and $B_2$ coefficients can be determined by numerical evaluation of the coefficients of the discrete Fourier series, as described by Budde (Photoelectric Analysis of Polarized Light, Applied Optics, Volume 1, Page 201 (1962), the teaching of which is incorporated herein by reference).

It is an outstanding feature of this invention to periodically provide an accurate updated measurement of the relative phase shift between the s and p polarization states of a monitoring beam of light during the deposition. Using the apparatus of FIG. 1, this is accomplished by directing the laser beam, which has a predetermined wavelength, into the thin film layers and detecting the portion of the light which is reflected from the front and back surfaces of the thin film layers. The difference in phase between the s and p polarized components of the reflected light is obtained from the ellipsometric measurement using the $B_2$ component of Equation (1). The thicknesses of the film at which the difference in phase between the s and p components is zero are known. Thus, the points at which the $B_2$ parameter is equal to zero can be determined to be thicknesses which are an integral multiple of one fourth of the wavelength of the monitoring light in the thin film.

This technique was experimentally verified in a thin film growth chamber with an ellipsometer placed so that the incident beam struck the growing film at an angle of 60 degrees with respect to the normal to the film surface. The light source used for the ellipsometer was a helium-neon laser operating at a wavelength of 0.6328 microns. With these parameters, the ellipsometer was capable of measuring the thickness of a thin film layer with a thickness of 0.1755 microns, which is the halfwave thickness for the ellipsometer. Thus, as the filter was fabricated, it would become a high reflector for the light beam from the ellipsometer.

Figure 2A:
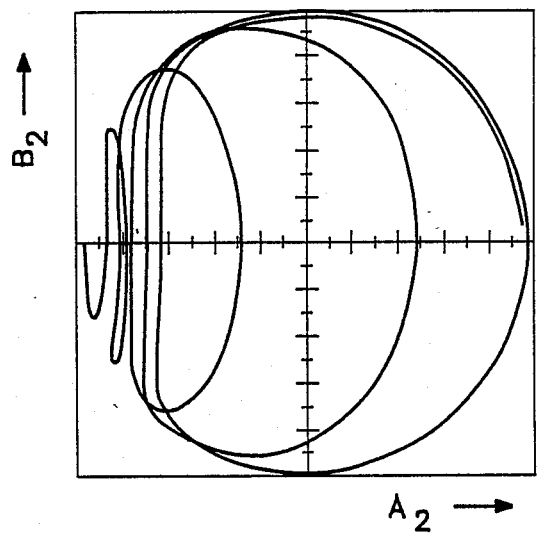
FIG. 2 is a plot depicting the progressive change which occurs in the $A_2$ and $B_2$ ellipsometric parameters as a thin film filter is fabricated.
Figure 2B:
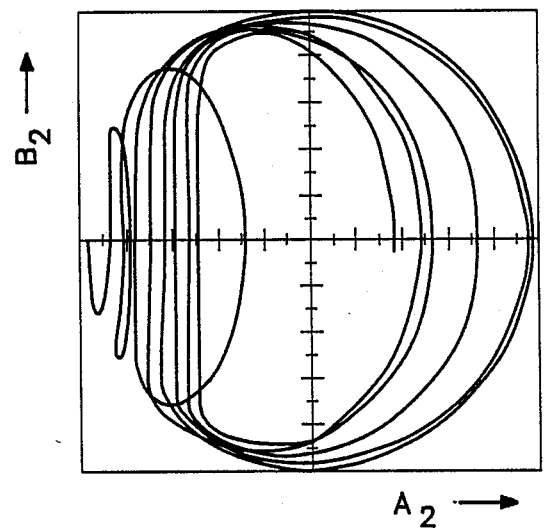

FIG. 2 is a plot depicting the progressive change which occurred in the $A_2$ and $B_2$ ellipsometric parameters as the filter was fabricated. The $A_2$ parameter is plotted along the horizontal axis, while the $B_2$ parameter is plotted along the vertical axis. FIG. 2a depicts the situation after the deposition of ten quarterwave layers, while FIG. 2b shows the cumulative variation which occurred in the parameters after 16 quarterwave layers. These plots are for a filter fabricated with two materials, the high index material having a refractive index of 2.13 and the low index material having an index of 1.53. The filter was deposited on a substrate of fused silica with an index of 1.455. Every time the $A_2$, $B_2$ plot crosses the horizontal axis, $B_2$ passes through zero and the phase difference between the s and p components of the reflected light is either 0 or 180 degrees. Likewise, whenever the structure consists of an integer number of quarterwave layers, the phase difference between the s and p polarizations will equal zero. Thus, each point at which an integer number of layers have been deposited can be correlated to a point when the $B_2$ parameter passes through zero.

Figure 3:
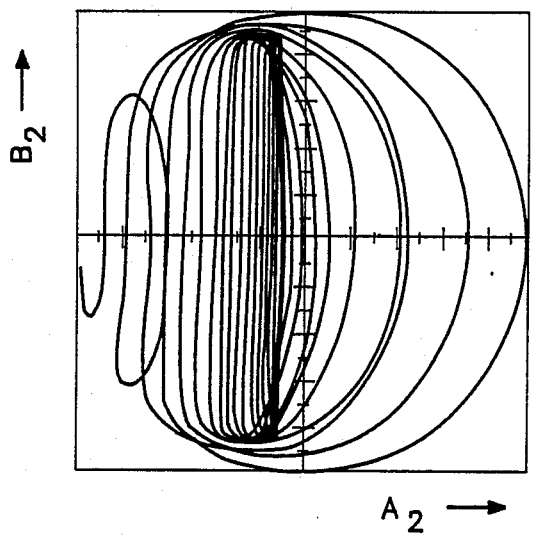
FIG. 3 is a plot of the $A_2$ and $B_2$ ellipsometric parameters similar to FIG. 2, but for a much higher number of layers.

The measurement technique of this invention is particularly useful because it can be used to make measurements with high accuracy even after many layers of a film have been deposited. FIG. 3 is a plot of the $A_2$ and $B_2$ ellipsometric parameters similar to FIG. 2, but for a much higher number of layers. It can be seen from FIG. 3 that the variation in the $A_2$ parameter approaches zero as the deposited layers cause the film to become a more efficient reflector of light at the monitoring wavelength. This is because the $A_2$ parameter is a measure of the difference in the s and p reflectivities, both of which approach unity as the number of layers increases. The $B_2$ parameter, however, continues to display a substantial amplitude in its variation and thereby provide a clear indication of the phase information needed to make thickness determinations.

Figure 4:
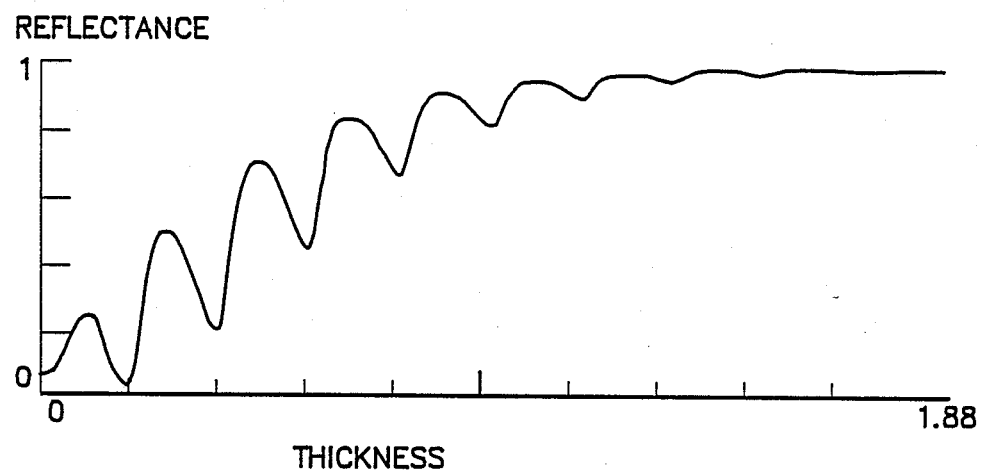
FIG. 4 is a plot of the reflectance of a monitoring beam from a thin film layer plotted as a function of the thickness of the depositing layer.

FIG. 3 should be contrasted with FIG. 4, which is a plot of the reflectance of a monitoring beam from a thin film layer plotted as a function of the thickness of the depositing layer, which is a typical measurement used in prior art techniques requiring the maxima or minima in the reflectance measurement to be determined. As can be seen from FIG. 4, as the layer increases in thickness, the maxima and minima become almost impossible to determine.

Figure 5:
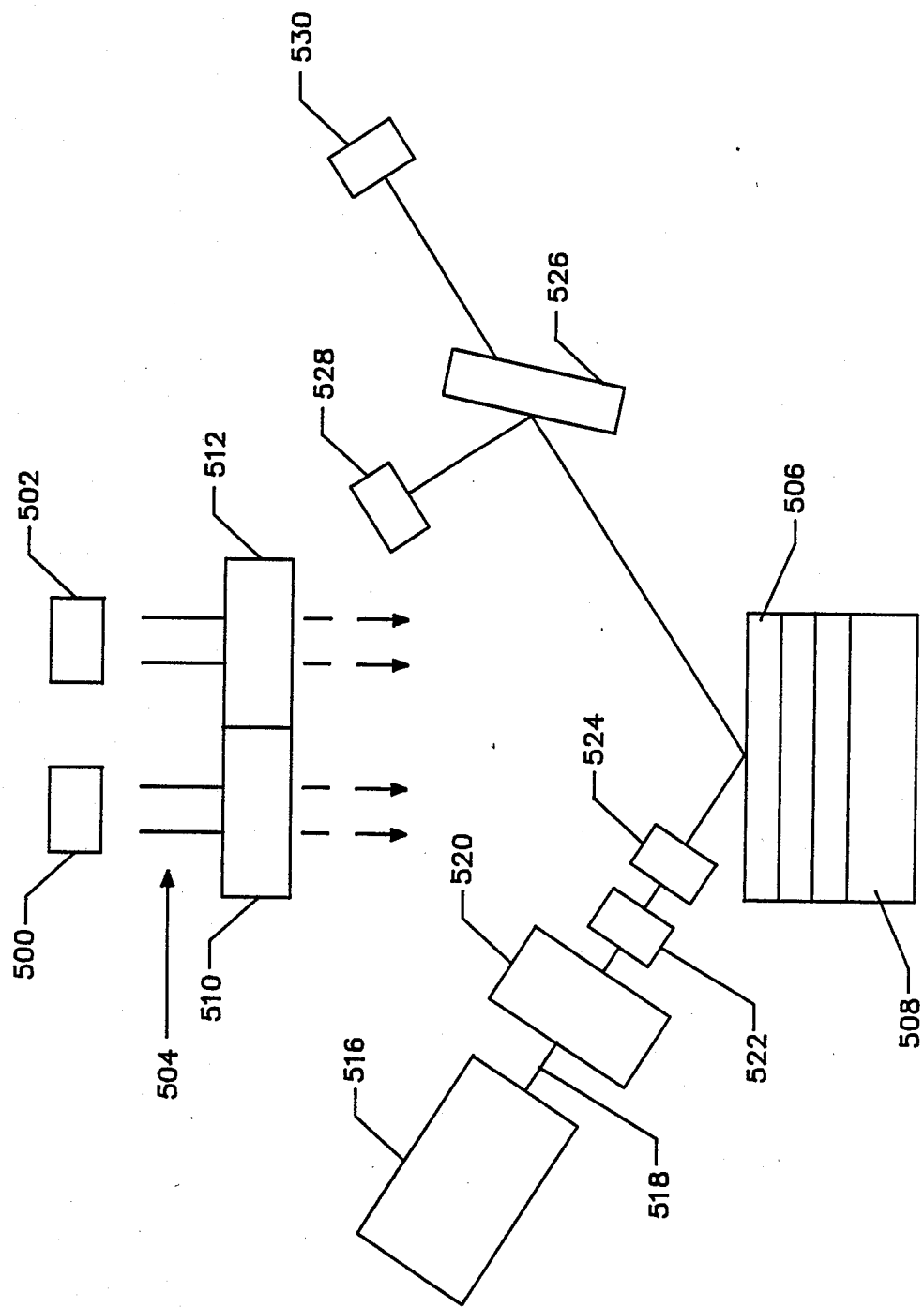
FIG. 5 is a schematic diagram similar to that of FIG. 1 but illustrating another embodiment of a phase measurement apparatus for practicing the invention.

This invention may also be achieved without using an ellipsometer, as depicted in FIG. 5, which is a schematic diagram similar to that of FIG. 1 but illustrating another embodiment of a phase measurement apparatus for practicing the invention. In FIG. 5, sources 500 and 502 are energized, as by heating, to release material, indicated by the arrows 504, which is deposited in thin layers, such as the layer 506, on a substrate 508. The substrate can be selectively shielded from the sources 500 and 502 by the shutters 510 and 512. A source of light 516 is used to direct a light beam 518 toward the layer 506. A monochromator 520 limits the portion of the beam 518 reaching the layer to a particular wavelength which can be selected by adjustment of the monochromator. A linear polarizer 522 and a quarter-wave plate 524 convert the beam 518 into circularly polarized light. The light beam 518 then impinges on the layer at a fixed angle of incidence. The reflected portion of the light is divided into two portions by a polarizing beam splitter 526. The beam splitter is rotated about the axis of the reflected beam so that the beam is divided into a component polarized at +45° with respect to the p polarization direction of the reflected beam and a component polarized at −45° with respect to the p polarization. Two detectors 528 and 530 indicate the amount of each component in the reflected light. When the amounts are equal, the phase shift is zero and the thickness of the layer 506 is an integral multiple of one fourth the wavelength of the particular light selected by the monochromator 520. A particular advantage of this embodiment of the invention is that the monochromator can be used to select a particular wavelength so that the technique can be adjusted to provide a quarterwave measurement at any desired thickness of the film being deposited.

One example of a thin film deposition task for which this invention is particular advantageous is the fabrication of a laser mirror which is intended to be used with the laser beam impinging at other than normal incidence. With conventional optical monitoring, each layer in such a mirror would have to be deposited slightly thicker than a quarterwave in order to allow for the shift to shorter wavelength with increasing angle of incidence. In addition, the additional thickness needed would be greater for the low index layers than for the high index layers. If, however, such a film were deposited using the phase sensitive monitoring of this invention with the incident monitoring beam set at the angle of incidence at which the mirror was to be used, no such correction would be required. This advantage, in addition to the ease and precision with which the zero crossing of the phase difference can be detected as compared to the standard optical monitoring technique of determining a maximum or minimum, makes the invention especially useful in such a deposition environment.

In conclusion, a unique ellipsometric technique has been developed to accurately measure the thickness of thin film layers. The preferred embodiments of this invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

I claim:

1. A method of monitoring the thickness of a growing layer during the fabrication of an optical thin film, comprising the steps of:
    directing a beam of circularly polarized monochromatic monitoring light, having an s polarized component with a first phase and a p polarized component with a second phase, into the layer;
    detecting the portion of the monitoring light reflected from the layer;
    measuring the difference in phase between the s and p polarized components of the reflected light; and
    relating those thicknesses of the layer at which the difference in phase between the s and p components is zero to thicknesses which are an integral multiple of one fourth of the wavelength of the monitoring light in the layer.

2. The method of claim 1, wherein the step of measuring the difference in phase between the s and p polarized components further comprises the steps of:
    dividing the portion of the monitoring light reflected from the layer into a component polarized at +45° with respect to the p polarization direction of the reflected light and having a first intensity and a component polarized at −45° with respect to the p polarization direction of the reflected light and having a second intensity;
    detecting the intensity of the +45° polarized component;
    detecting the intensity of the −45° polarized component; and
    comparing the +45° polarized intensity to the −45° polarized intensity to determine the difference in phase between the s and p polarized components.

* * * * *